(12) United States Patent
Pscherer et al.

(10) Patent No.: US 9,985,372 B2
(45) Date of Patent: May 29, 2018

(54) TERMINAL PIN AND FEEDTHROUGH

(71) Applicant: BIOTRONIK SE & Co. KG, Berlin (DE)

(72) Inventors: Norbert Pscherer, Fuerth (DE); Daniel Kronmueller, Nuremberg (DE); Josef Teske, Hallstadt (DE)

(73) Assignee: BIOTRONIK SE Co. KG, Berlin (DE)

( * ) Notice: Subject to any disclaimer, the term of this patent is extended or adjusted under 35 U.S.C. 154(b) by 163 days.

(21) Appl. No.: 15/051,902

(22) Filed: Feb. 24, 2016

(65) Prior Publication Data

US 2016/0276769 A1    Sep. 22, 2016

Related U.S. Application Data

(60) Provisional application No. 62/135,710, filed on Mar. 20, 2015.

(51) Int. Cl.
| | | |
|---|---|---|
| *A61N 1/37* | (2006.01) | |
| *H01R 13/03* | (2006.01) | |
| *A61N 1/375* | (2006.01) | |
| *H01G 4/35* | (2006.01) | |

(52) U.S. Cl.
CPC .......... *H01R 13/03* (2013.01); *A61N 1/3754* (2013.01); *H01G 4/35* (2013.01); *H01R 2201/12* (2013.01)

(58) Field of Classification Search
CPC .. H01R 13/03; H01R 2201/12; A61N 1/3754; H01G 4/35
See application file for complete search history.

(56) References Cited

U.S. PATENT DOCUMENTS

| | | | |
|---|---|---|---|
| 7,340,305 B2 | 3/2008 | Fischbach et al. | |
| 7,747,321 B2 | 6/2010 | Fischbach et al. | |
| 2011/0232961 A1* | 9/2011 | Teske | A61N 1/3754 174/650 |
| 2011/0303458 A1* | 12/2011 | Sutay | H01G 4/232 174/650 |
| 2013/0176658 A1 | 7/2013 | Iyer et al. | |

FOREIGN PATENT DOCUMENTS

EP    1 695 736    8/2006

OTHER PUBLICATIONS

European Search Report and Annex to the European Search Report on European Patent Application No. EP 16 15 7264, dated Aug. 29, 2016 (5 pages).

* cited by examiner

*Primary Examiner* — Rex R Holmes
(74) *Attorney, Agent, or Firm* — Buchanan Ingersoll & Rooney PC

(57) ABSTRACT

A terminal pin for electrically connecting a conductor support, wherein the terminal pin is provided for the bonded connection to a conducting surface of the conductor support, is formed from a biocompatible non-noble metal, has a section at or near one end that is thickened relative to a section located further from the end, and at least one part of the surface of the thickened section has a soft-solderable coating of a noble metal.

16 Claims, 3 Drawing Sheets

TERMINAL PIN AND FEEDTHROUGH

CROSS-REFERENCE TO RELATED APPLICATIONS

This patent application claims the benefit of U.S. Provisional Patent Application No. 62/135,170, filed on Mar. 20, 2015, which is hereby incorporated by reference in its entirety.

TECHNICAL FIELD

The present invention relates to a terminal pin for electrically connecting a conductor support, which is provided for the bonded connection to a conducting surface of the conductor support. The present invention also relates to a feedthrough of an implantable electromedical device (IMD) and, finally, to such a device as a whole.

BACKGROUND

Most of the implantable electromedical devices (IMDs) that have practical significance are intended to emit electrical pulses to excitable bodily tissue via suitably placed electrodes. Furthermore, many devices can measure electrical pulses and stimuli in the body of the patient in a targeted manner and record or evaluate these electrical pulses and stimuli over a relatively long period of time in order to select an individualized treatment and perform an in vivo check of the success of the treatment.

In order to carry out these functions, electronic/electrical functional units for generating and measuring the pulses and for suitably controlling the pulse generation are accommodated in the housing of the device, and electrodes or connections for at least one electrode lead, in the distal end section of which the electrodes for transmitting pulses to the tissue are accommodated, are provided directly on the outside of the device. The electronic/electrical functional units in the interior of the housing are intended to be connected to the outer electrodes or electrode lead connectors in a manner that ensures functionality that is absolutely and permanently reliable under the special conditions of the implanted state.

This task is performed by so-called feedthroughs, which are the subject of numerous and highly diverse developments. The task of a feedthrough is that of routing the electrical signals through the hermetically sealed housing and, thereby, enabling electrical contact to be established between the electronics in the hermetically sealed housing and the electrodes in the body of the patient. Terminal pins are used for this purpose in many such feedthroughs, which are contacted in the housing interior to the printed circuit board or a similar conductor support that is located there and route the signals through the housing.

In conjunction with the trend toward miniaturization and the advances made in electronics, rapid transformations have taken place in soft soldering technology (solder) in recent years. Manual assembly processes were increasingly replaced by fully automated pick-and-place machines, and through-hole technology (THT) was gradually replaced by surface-mount technology (SMT). This makes it possible to design smaller, more compact circuits and, therefore, also incrementally results in smaller, more patient-compatible IMDs. In order to achieve the numerous advantages of SMT, feedthroughs must meet the requirements placed on a surface-mount device (SMD). To this end, in particular, the pin that is used, which is usually soldered-in (e.g., brazed) in a high-temperature process, must meet high electrical, thermal, and mechanical requirements before it can be soldered onto the printed circuit board or conductor support. The reliability of all joints of the feedthrough must be ensured over the entire lifespan, also under the influence of bodily fluids.

For this reason, there are terminal pins that are made entirely of a noble metal (such as, for example, platinum, platinum-iridium, palladium), which can be easily and reliably connected to the conductor support in a soft soldering process, although the high price thereof is disadvantageous. Moreover, there are multi-component arrangements comprising, for example, the actual terminal pin and a soft-solderable additional component (e.g., pad, barrel) made of different materials.

The latter solutions require a separate assembly and production step. Components are provided, which are joined with the feedthrough after or during the high-temperature soldering (e.g., brazing). The additional assembly outlay is not inconsiderable. It can cause the production costs for the additional components to exceed the material value thereof by several-fold. The additional components are usually very small and delicate (typically <1 mm) and, therefore, are difficult to place and orient. Furthermore, separate production tools are required to install the additional components. Before assembly, the components must be additionally stored and tested, and they require additional lot management and tracking.

The additional joining process may result in rejects. If the process of joining the pin with components is carried out integrally with the joining process of the feedthrough, an additional screening inspection must be carried out, in which the process of the pin joining is assessed. After the joining, the connection point must be inspected for adhesion, sufficient stability, and service life. It is entirely possible that the components of the pin can tilt and become displaced, resulting in displacement when placed on the printed circuit board. This must be detected in a separate test step and must be avoided and tested in the feedthrough assembly.

U.S. Pat. No. 7,340,305 discloses a feedthrough of an IMD, in which terminal pins are used that have a core that is not based on expensive platinum, platinum-iridium, or palladium and that have a single- or multi-component, conductive coating. The coating makes it possible, on the one hand, to control and/or limit oxidation of the terminal pin under the conditions in which an implanted device is used, and, on the other hand, to connect the terminal pin to a printed circuit board by means of a soft-soldering process. United States Publication No. 2011/0303458 also discloses terminal pins having a partially multi-layer design and the use thereof in feedthroughs of IMDs.

U.S. Pat. No. 7,747,321 discloses, as shown in FIG. 1 thereof, a cardiac pacemaker 1 having a pacemaker housing 3 and a header 5, in the interior of which other electronic components, as well as a printed circuit board (PCB) 7, are disposed, wherein an electrode lead 9 is connected to the (non-illustrated) lead terminal of said cardiac pacemaker, said lead terminal being disposed in the header. A feedthrough 11 provided between the device housing 3 and the header 5 comprises a plurality of terminal pins 13. The terminal pins are inserted, at one end, through a corresponding via in the printed circuit board and are soft-soldered therewith. Said terminal pins have a wire core, which is made of tantalum, niobium, titanium, molybdenum, or copper, for example, and an oxidation-resistant sheathing made of a biocompatible material, such as gold, platinum, titanium, or the like.

The present invention is directed toward overcoming one or more of the above-mentioned problems.

SUMMARY

A problem addressed by the present invention is that of providing a terminal pin that is improved as compared to known arrangements, said terminal pin being inexpensive to manufacture and process, in particular, and the use of which makes it possible to reduce the test and assembly effort when carrying out the surface mounting (SMT) of feedthroughs.

At least this problem is solved by a terminal pin having the features of claim 1. Advantageous developments of the inventive idea are the subject matter of the dependent claims. The present invention additionally provides a feedthrough having the features of claim 16.

According to the present invention, the terminal pin has a region at or near one end that is thicker than a section further from the end and at least one part of the surface of the thickened section has a soft-solderable coating comprising a noble metal. According to a first aspect of the present invention, the result thereof is that the proposed terminal pin can be joined on a typical SMD printed circuit board, or a similar conductor support, by means of an established soft soldering process, wherein the soldering process is compatible with established processes and materials and yields a connection that is stable over the long term.

This ensures high dimensional stability and reproducibility in the manufacture of the connection and/or—according to a second, relatively independent aspect of the present invention—makes it possible to obtain a diffusion-inhibiting constriction in the longitudinal course of the terminal pin and, therefore, in the region of a feedthrough formed with such a pin.

As compared to established configurations containing multi-component terminal pins, the following special advantages result:

integration of a plurality of components into one component, less expensive production without redesigning the products or redeveloping the products, fewer rejects, less assembly effort, which results in lower costs, and greater dimensional accuracy and registration.

In one embodiment of the present invention, the thickened section is formed on the end of the terminal pin with rotational symmetry, substantially in the manner of a nail head. This embodiment can be manufactured very easily and inexpensively using the long-established upset forming process and, depending on the specific design, offers the possibility to particularly easily adapt the end surface of the terminal pin to the base area that is available for the connection to the corresponding track.

In another embodiment of the present invention, the shape at the end of the pin is adapted to the land pattern of the printed circuit board (PCB). Base areas that are known and frequently used are rectangles, hexagons, and octagons or other polygons. In order to be capable of ensuring that the product can be easily manufactured, the corners of the shaping tool must be rounded so that the pin can be removed from the mold after shaping. The contact area between the feedthrough pin and the printed circuit board is enlarged, thereby making it possible to lower the transition resistance and increase the loadability of the interconnection between the pin and the printed circuit board.

In one configuration of this embodiment, a tip section that is conical, hemispherical, or cylindrical, in particular, is formed on the outermost end of the terminal pin. Such an additional geometry on the underside of the pin, which performs the function of an area of contact on the printed circuit board, is advantageous for the following reasons: (1) The pin must not have all-over contact with the printed circuit board during the soft soldering process. (2) A defined capillary gap forms between the pin and the printed circuit board, into which liquid soft solder can seep and/or in which solder paste is not fully displaced and/or remains at defined points when the feedthrough and the other components is placed into the solder paste.

Moreover, it can be advantageous to design the pin ends to be pointed or sharp-edged so that these can be centered and/or fixed in the substrate material of the printed circuit board (PCB) by being pressed in a defined manner. It is thereby ensured that the feedthrough does not float or slip in the solder paste during the process in the reflow oven. Soldering defects, such as, for example, side or tip overhang, can therefore be effectively reduced. As a result, the process can take place with typical process parameters, even if the center of mass and/or the moment of inertia of the feedthrough are atypical for SMD components due to the design.

In an embodiment according to a second aspect of the present invention, the thickened section is defined relative to a section that is located further from the end and has a diameter that is reduced compared to the diameter that the terminal pin has in the larger portion of the longitudinal extension thereof. In particular, the section that is thickened as compared to the section further from the end having the reduced diameter has the same diameter as the terminal pin in the larger part of the longitudinal extension thereof. This merely requires that a constriction be formed in the longitudinal extension of the terminal pin, in a simple stretching or rolling step, for example.

The aforementioned embodiments can be combined with one another; in particular, in one embodiment, the section that is located further from the end and has the reduced diameter is formed directly adjacent to or with predefined spacing from the nail-head type end section of the terminal pin. As a result, the effects according to the first and the second aspect of the present invention can also be combined in a synergistic manner, wherein the presetting of a desired spacing between the nail-head end and the constriction of the terminal pin permits a precise adaptation to the geometric configuration of the printed circuit board relative to the feedthrough.

In one embodiment, the effects mentioned further above can be simplified, especially with regard to the second aspect of the present invention, by providing the terminal pin with a plurality of thickened and coated sections. In this connection, it can be especially provided that at least one part of the plurality of thickened and coated sections is provided with a continuous coating, which extends over sections that are located there between and have a smaller diameter.

In general, the coating can cover the entire surface of the thickened section or of every thickened section, which makes it possible to produce the coating in a technologically particularly simple manner. On the other hand, it can be expedient that the coating cover only the bottom and, optionally, the periphery or subsections of the periphery of the nail-head type, thickened section. The coating can comprise one or more thin layers, which can also be placed one on top of the other in a process. A coating can result in the advantageous implementation of a direct soft soldering of the terminal pin to the conductor support or also the bonding of connecting wires to the terminal pin.

In another embodiment of the present invention, the pin has a plurality of bends or roundings along the axis thereof. The bend can be produced during a shaping process. In particular, after the pins have been joined to a feedthrough, the pins can be very easily oriented and/or shaped. This makes it possible for the pins of the feedthrough to emerge from the housing not parallel to the printed circuit board, but rather at any angle, e.g., 90°, relative to the printed circuit board.

It is conceivable that biocompatible, conductive materials (e.g., titanium, tantalum, and niobium) are used as the material of the untreated pin. As an alternative, the terminal pin can be manufactured from an inexpensive substrate (e.g., copper, constantan, nickel). In the embodiment involving non-biocompatible material, the pin is initially shaped and then coated with a biocompatible material (e.g., titanium, tantalum, niobium, platinum, palladium, or alloys thereof). The coating must comprise at least the part that is not located within the housing of the eventual IMDs.

In order to establish the electrical connection, according to another embodiment, an easily soft-solderable surface is exposed on the pin in the direct proximity of the thickening, e.g., by means of a flux or by preparing the surface (plasma activation or etching).

The soft-solderable coating can contain at least one noble metal or one of the metals nickel, copper, silver, tin, or an alloy having at least one of these metals. Typical layer thicknesses are a few micrometers. Related metals may also be used, such as one or more of the elements iridium, rhodium, or ruthenium, for example. It goes without saying that highly diverse alloys of at least two of the elements mentioned here, advantageously, in particular, alloys that are commercially available at relatively low cost, can also be used in the embodiment of the present invention. As the material of the untreated terminal pin and/or the pin body, it is conceivable, in particular, to use copper or titanium, as well as elements such as tantalum, niobium, or molybdenum, as well as alloys thereof.

In another embodiment, which fits in the context of the second aspect of the present invention, in particular, a directly touching layer of the coating is designed as a diffusion barrier, and said diffusion barrier has, in particular, at least one of the metals aluminum, nickel, or gold. The diffusion barrier can be applied over or under the soft-solderable coating. It can also be reasonable to produce a plurality of diffusion barriers, which are applied on top of one another and to combine these or to coat these on top of one another in order to obtain a particularly long service life of the feedthrough that is formed with such a terminal pin.

According to a technological embodiment of the present invention, the coating or at least one layer thereof is designed as a galvanic coating or as a thin layer that is produced by means of a vacuum coating process. Expedient layer thicknesses are between 0.1 μm (for a thin-layer method) and 10 μm (for a galvanic method). Both of the embodiments have specific advantages and disadvantages; for example, the application of a layer is highly selective in galvanization, but the layer is often contaminated with foreign materials from the galvanic bath. Sputtering under vacuum takes place on all sides, although with very high purity.

In order to protect the coating from impurities, contamination, and oxidation, the coating on the tip can be sealed until further processing is carried out. A polymer or an organic protective film (OSP—Organic Surface Protection) can be used for this purpose. Known protective films (e.g., Glicoat, ENTEK+) can be applied completely or selectively onto the soft-solderable layer or the entire pin. Typical layer thicknesses are 0.2 μm to 0.6 μm and contain, for example, substituted imidiazole and/or triazole. The protective film prevents the oxidation of the base material during storage for several months, typically, and pyrolyzes immediately before or during the soft-soldering process. Combustion residues on the printed circuit boards can be removed in automated systems during the established wash process, without leaving residue.

Further embodiments, features, aspects, objects, advantages, and possible applications of the present invention could be learned from the following description, in combination with the Figures, and the appended claims.

DESCRIPTION OF THE DRAWINGS

Advantages and useful features of the present invention are also derived from the description of exemplary embodiments with reference to the Figures. In the Figures.

DETAILED DESCRIPTION

Figure 1:
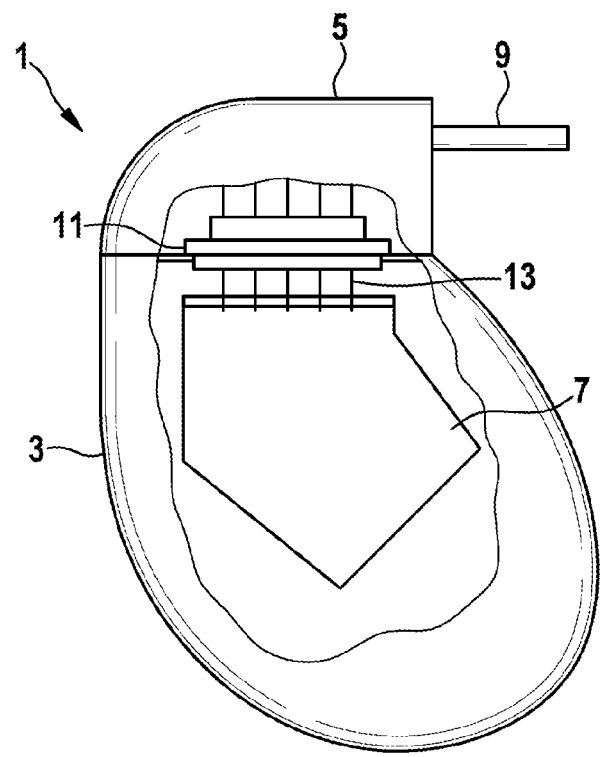
FIG. 1 shows a schematic illustration of a conventional cardiac pacemaker.

In all of the FIGS. 2 to 6, the terminal pin is labeled consistently with numerals 13 and 13', in accordance with FIG. 1 and independently of the deviating geometric shapes and arrangements of the coating, and the labeling of individual sections or the respective coating is selected accordingly.

Figure 2:
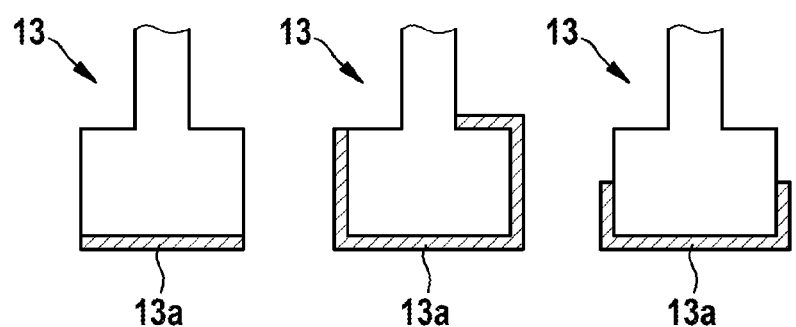
FIG. 2 shows schematic partial cross-sectional illustrations of terminal pins according to embodiments of the present invention.
Figure 2:
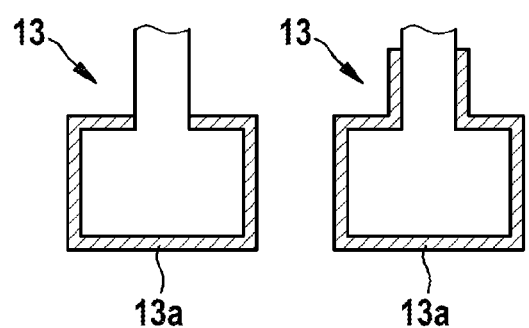

FIG. 2 shows a plurality of embodiments of a terminal pin 13 having a nail-head type end, wherein said embodiments differ by the extent of the applied, soft-solderable coating 13a. In the embodiment shown in the upper left, a coating 13a is provided only on the bottom of the nail head and, therefore, on the end-side face of the terminal pin, but in the variant shown to the right thereof, said coating extends around the periphery of the nail-head type, thickened end section and, on one side, across the top surface of said end section, said top surface being disposed opposite the front surface. In the configuration shown in the upper right, however, the coating 13a extends only up to a predetermined height on the peripheral surface of the nail head, in the configuration shown in the lower left said coating extends over all surfaces of the nail head, and in the configuration shown in the lower right, said coating even extends slightly into the unworked longitudinal extension of the terminal pin.

Figure 3:
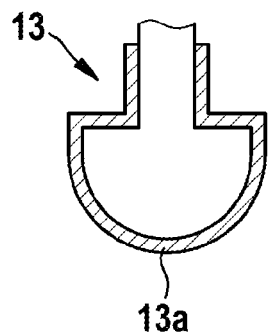
FIG. 3 shows a partial cross-sectional illustration of a terminal pin according to another embodiment of the present invention

FIG. 3 shows another terminal pin having a nail-head type thickening of the outermost end, which is hemispherical in this case, however. This configuration can be formed by means of an appropriate shaping tool.

Figure 4:
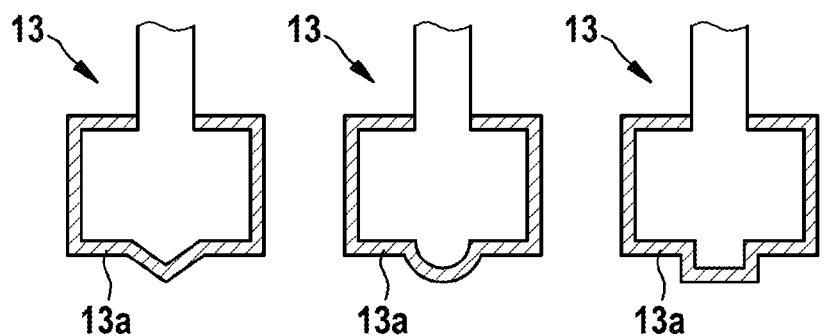
FIG. 4 shows schematic partial cross-sectional illustrations of terminal pins according to other embodiments of the present invention.
Figure 4:
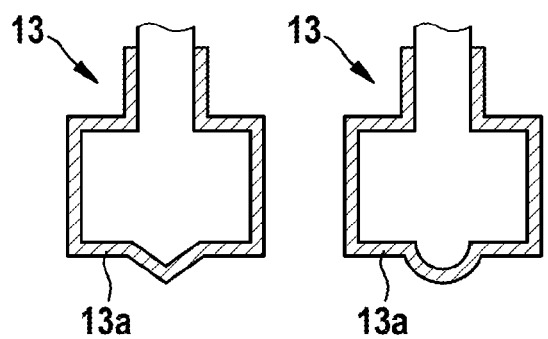
Figure 4:
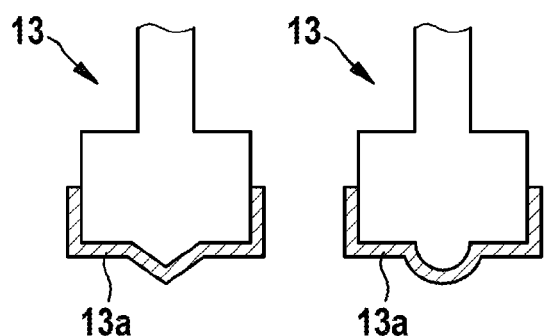

FIG. 4, which is based on FIG. 3, shows a plurality of embodiments of a nail-head type terminal pin 13, which is thickened on the end, wherein the embodiments in the left column are characterized by a conical tip extending out of the bottom of the nail head, the embodiments in the middle column are characterized by a hemispherical shape protruding from the bottom of the nail head, and the embodiment in the upper right is characterized by a cylindrical shape protruding from the bottom of the nail head. Different coating variants are shown, which are self-explanatory with reference to FIG. 3 and are therefore not further described.

Figure 5:
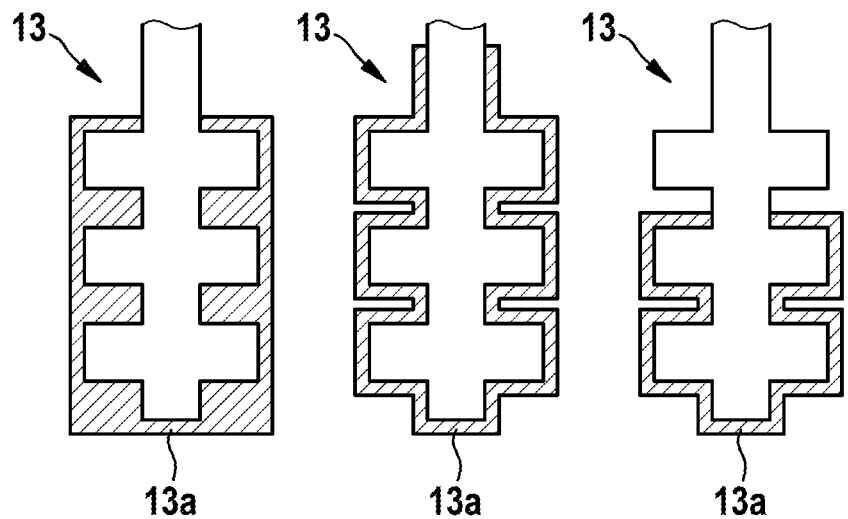
FIG. 5 shows schematic partial cross-sectional illustrations of terminal pins according to other embodiments of the present invention.

FIG. 5 shows three coating variants of another embodiment of the terminal pin 13, in which three disk-shaped thickenings are provided in succession. In the embodiment shown at the very right, only the pin end and two of the thickenings are provided with a continuous coating 13a, while the coating in the middle variant extends over all three thickenings and slightly into the adjoining terminal-pin portion having a smaller diameter. The left-most embodiment differs from the others in that the coating 13a is formed such that said coating encloses the end of the terminal pin 13 in the manner of a cylinder, i.e., there are no annular grooves located between the disk-shaped thickenings, in contrast to the other two embodiments.

Figure 6:
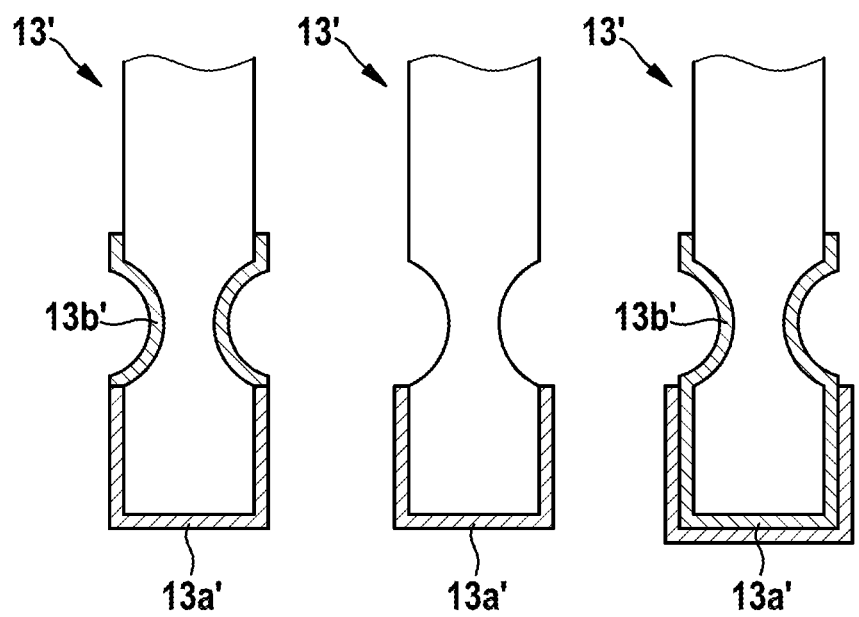
FIG. 6 shows schematic partial cross-sectional illustrations of terminal pins according to other embodiments of the present invention.

FIG. 6 shows three coating variants of a terminal pin 13', in the case of which, in contrast to the terminal pins 13 according to FIGS. 2 to 5, a thickening is not formed in the end section but, rather, a section having a reduced diameter is present and is spaced apart from the pin end. In comparison thereto, the direct pin end is therefore a thickening in the sense of the general embodiments described above. In the configuration shown on the left in FIG. 6, the region having a reduced diameter is covered with a diffusion barrier layer 13b', while the end section of the pin, including the end-side face, is provided with a soft-solderable coating 13a'. In the middle embodiment, only the soft-solderable coating 13a' of the end section is provided, while the section that is further from the end and has a smaller diameter is uncoated. In the configuration shown on the right, the entire pin end, i.e., the section having the reduced diameter as well as the end section and the face, is initially provided with a diffusion-inhibiting coating 13b', and in the thickened region of the pin end, the first layer is also covered with a second layer (cover layer) 13', which is soft-solderable.

The embodiment of the present invention is possible in various other embodiments and in highly diverse combinations of the features that are described above as features of various embodiments, in particular, also with more than two-component and/or two-layer coating systems, having materials other than those mentioned above, and in various geometric configurations of the respective thickenings and/or regions that are further from the end and have a smaller diameter.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A terminal pin for electrically connecting a conductor support, wherein the terminal pin is provided for a bonded connection to a conducting surface of the conductor support, and is formed at least in sections from a biocompatible, non-noble metal, and has a section at or near one end that is thickened relative to a section located further from the end, and at least one part of the surface of the thickened section has a soft-solderable coating, wherein the sections of the terminal pin are integrally formed.

2. The terminal pin according to claim 1, wherein the thickened section is formed on the end of the terminal pin with rotational symmetry, or as a quadrangular or polygonal prism or a four- or multi-sided truncated pyramid, substantially in the manner of a nail head.

3. The terminal pin according to claim 2, wherein a tip section is formed on the bottom of the nail head, and therefore on the outermost end of the terminal pin, which is conical, hemispherical, cylindrical, or pyramid-shaped.

4. The terminal pin according to claim 1, wherein the thickened section is defined relative to a section that is located further from the end and has a diameter that is reduced compared to the diameter that the terminal pin has in a larger portion of a longitudinal extension thereof.

5. The terminal pin according to claim 4, wherein the section that is thickened as compared to the section further from the end having the reduced diameter has the same diameter as the terminal pin in the larger portion of the longitudinal extension thereof.

6. The terminal pin according to claim 4, wherein the section that is located further from the end and has the reduced diameter is formed directly adjacent to or with predefined spacing from a nail-head type end section of the terminal pin.

7. The terminal pin according to claim 1, further comprising a plurality of thickened and coated sections.

8. The terminal pin according to claim 7, wherein at least one part of the plurality of thickened and coated sections is provided with a continuous coating, which extends over sections that are located there between and have a smaller diameter.

9. The terminal pin according to claim 1, wherein the coating covers the entire surface of the thickened section or each thickened section.

10. The terminal pin according to claim 2, wherein the coating covers only the bottom and the periphery or subsections of the periphery of the nail-head type, thickened section.

11. The terminal pin according to claim 1, wherein the coating comprises at least one of gold, platinum, copper, silver, nickel, iridium, and palladium.

12. The terminal pin according to claim 1, wherein the coating comprises multiple layers and, in particular, has a cover layer of at least one of gold, platinum, copper, silver, nickel, iridium, and palladium.

13. The terminal pin according to claim 12, wherein a layer of the coating that directly touches the non-noble metal of the terminal pin is designed as a diffusion barrier and, in particular, comprises at least one of the metals aluminum, nickel, molybdenum, or gold.

14. The terminal pin according to claim 1, wherein the coating or at least one layer thereof is designed as a galvanic coating or as a thin layer that is produced by means of a vacuum coating process.

15. The terminal pin according to claim 1, further comprising at least one section that has a coating of a biocompatible material, including titanium, tantalum, niobium, gold, platinum, palladium, or an alloy of at least one of these metals.

16. A feedthrough of an implantable electromedical device including a cardiac pacemaker or cardioverter, which comprises at least one terminal pin according to claim 1.

* * * * *